United States Patent
Engelson et al.

[11] Patent Number: 6,030,369
[45] Date of Patent: *Feb. 29, 2000

[54] MICRO CATHETER SHAFT

[75] Inventors: Erik T. Engelson, Menlo Park; Mark Carter, Fremont, both of Calif.

[73] Assignee: Target Therapeutics Inc., Fremont, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/887,950

[22] Filed: Jul. 3, 1997

[51] Int. Cl.⁷ .............................. A61M 5/00; A61M 25/00
[52] U.S. Cl. ........................... 604/264; 604/523; 604/525
[58] Field of Search ..................................... 604/264, 280, 604/281, 915; 600/139, 140, 433–435, 523, 525, 534

[56] References Cited

U.S. PATENT DOCUMENTS

| | | |
|---|---|---|
| 3,752,617 | 8/1973 | Burlis et al. . |
| 4,211,741 | 7/1980 | Ostoich . |
| 4,250,072 | 2/1981 | Flynn . |
| 4,282,876 | 8/1981 | Flynn . |
| 4,385,635 | 5/1983 | Ruiz . |
| 4,596,563 | 6/1986 | Pande . |
| 4,627,844 | 12/1986 | Schmitt . |
| 4,636,346 | 1/1987 | Gold et al. . |
| 4,753,765 | 6/1988 | Pande . |
| 4,775,371 | 10/1988 | Mueller, Jr. . |
| 4,904,431 | 2/1990 | O'Maleki . |
| 4,994,047 | 2/1991 | Walker et al. . |
| 5,085,649 | 2/1992 | Flynn . |
| 5,125,913 | 6/1992 | Quackenbush . |
| 5,308,342 | 5/1994 | Sepetka et al. . |
| 5,360,389 | 11/1994 | Chenette ................................. 600/34 |
| 5,380,307 | 1/1995 | Chee et al. . |
| 5,437,632 | 8/1995 | Engelson . |
| 5,533,985 | 7/1996 | Wang . |
| 5,538,510 | 7/1996 | Fontirroche et al. .................... 604/265 |
| 5,542,937 | 8/1996 | Chee et al. . |
| 5,599,326 | 2/1997 | Carter . |
| 5,676,659 | 10/1997 | McGurk ................................. 604/282 |

Primary Examiner—Corrine McDermott
Assistant Examiner—Michael J. Hayer
Attorney, Agent, or Firm—Morrison & Foerster LLP

[57] ABSTRACT

This is a catheter having a shaft, the layers of which are coextruded in an intermittently changing pattern that produces particular mechanical and frictional properties in the structure. The outer layer of the catheter shaft is comprised of a material which has greater flexibility than the material which comprises the inner layer of the catheter shaft. The stiffer material which comprises the inner layer has frictional properties which facilitate guidewire passage and control. The invention includes the substituent shaft per se and a method of making the shaft.

18 Claims, 4 Drawing Sheets

MICRO CATHETER SHAFT

FIELD OF THE INVENTION

This invention is a surgical device. In particular, it is a catheter having a shaft, the layers of which are coextruded in an intermittently changing pattern that produces particular mechanical and frictional properties in the structure. The outer layer of the catheter shaft is comprised of a material which has greater flexibility than the material which comprises the inner layer of the catheter shaft. The stiffer material which comprises the inner layer has frictional properties which facilitate guidewire passage and control. The invention includes the substituent shaft per se and a method of making the shaft.

BACKGROUND OF THE INVENTION

Catheters are used in a variety of procedures to treat vascular maladies throughout the body. Catheters are used to place various treatment materials, drugs, and devices within remote regions of the human body. Catheters with distal balloons are used to treat narrowed regions in the arterial system via percutaneous translumenal coronary angioplasty (PTCA) by expanding the balloon in the region of the plaque narrowing the lumen and pressing that plaque into the vessel wall.

In virtually any of these catheters, the distal end is more flexible than the proximal end and, in the more sophisticated designs, these may be intermediate regions of intermediate flexibility. The construction of these devices has become increasingly more complicated. Catheter construction now often involves multiple layers of tubing, inclusion of braided stiffeners, coil stiffeners and the like. Coaxial inclusion of dissimilar materials such as polyimide tubing has also been the practice. Simplicity has not been the watchword of modern catheter construction. In particular, catheters using distal balloons (such as the PTCA catheter mentioned above) are even more complicated because of the need to include independent tubing with which to fill and to deflate the distal balloon.

U.S. Pat. No. 3,752,617, to Burlis, shows a method and apparatus for producing tubing having different characteristics along its axial length. In general, it shows procedures for making tubing either of a single composition of a mixture of polymers or tubing having coaxially placed inner and outer layers. The patent also suggests methods for changing the physical properties of the tube as it is extruded. In the first variation, there are two extruders, one for homogenizing and delivering a first polymer to a mixing die and a second extruder for homogenizing and delivering a second polymer to the same mixing die. A sequencing control provides, at various time intervals, an increased flow from one of the extruders and a proportionally increased flow from the other extruder. The mixture of the two polymers passes through the die and results in an extruded tubing having varying physical parameters along its axial length.

The second procedure involves a composite extrusion die which produces a tube having sections of exclusively one polymer and other sections of exclusively another polymer with intermediate sections having inner portions of one and outer portions of the other polymer.

U.S. Pat. No. 4,211,741, to Ostoich, also shows a method for extruding laminated medical-surgical tubing. In particular, the tubing is coextruded, multiple-layered medical tubing having a first layer of relatively inexpensive plastic material such as polyvinyl chloride and a second layer of polyurethane. A variation described therein shows the additional extrusion of polyurethane in a third layer onto the two-layer tubing mentioned just above.

U.S. Pat. No. 4,385,635, to Ruiz, shows an angiographic catheter having a soft, flexible, pliable leading tip zone, a main reinforced length, and an intermediate zone between the tip zone and the main length. The main length is made up of a polyamide such as Nylon, and the intermediate zone contains a polyamide which is tapered distally and is jacketed by polyurethane. The soft tip is wholly polyurethane. No procedure is given for producing the device disclosed there.

U.S. Pat. No. 4,775,371, to Mueller, Jr., shows a balloon catheter having a multilayered shaft. The shaft may be structured in such a fashion that the various layers taper axially in one fashion or another, typically to permit the distal section to be more flexible than the proximal section. However, rather than being coextruded, the various layers are independently extruded. The outer layer is of a polymer which may be shrunk onto the inner layer after placement on that inner layer.

U.S. Pat. No. 4,904,431, to O'Maleki, shows a method for manufacturing soft-tip catheters having inner rigid polymer layers and soft outer polymer layers. The procedure, however, involves the independent extrusion of the inner sheath with a separate pulling speed so to create depressions or breaks in the inner polymer layer. The inner polymer layer is fed to another extruder having an independently variable pull rate to extrude the softer material onto the outer surface of the inner layer. Wire meshes and the like may be introduced into the device at desired positions.

U.S. Pat. No. 4,994,047, to Walker et al., shows a swellable cannula formed of concentric inner and outer hydrophilic and substantially non-hydrophilic layer structures. A multilumen cannula is shown in FIG. 7 of the patent. The device does not appear to change in flexibility along its axial length. Further, it is not altogether clear what the procedure for creating the device is. The single description (column 9, lines 25–35) appears to suggest that co-extrusion was the chosen procedure.

U.S. Pat. No. 5,085,649, to Flynn, shows a multilayered catheter tubing material. The tubing is shown to have an inner layer of constantly diminishing thickness and an outer layer of constantly increasing thickness, resulting in a catheter body having a consistent diameter along its length. It is said (at column 4, lines 52 and following) that the material is made by discharging from an inner annular orifice of a bi-orifice extrusion head, a first inner resin layer and also discharging from a concentric outer annular orifice of the extruder head, an outermost resin layer. The feed rate of the first resin is supplied at a constantly decreasing rate, and the second resin is supplied to the extruder at an increasing rate inversely proportional to the declining rate of the first. The bi-orifice extrusion head is of the type shown in U.S. Pat. No. 4,282,876. No suggestion of multiple lumen material is shown.

U.S. Pat. No. 5,125,913, to Quackenbush, describes a double-layer medical catheter having an integral soft tip made by the co-extrusion of a relatively rigid inner layer and a relatively soft outer layer. The extrusion equipment is operated in such a fashion so to interrupt the supply of the material for the inner, relatively soft layer so to cause a periodic void in the inner wall as the assembly is extruded. The act of interrupting the supply is said to cause a ramp in inner wall thickness at the leading edge of each void. The void is then cut to produce two soft-tipped catheters.

This invention is a continuously extruded, multilumen catheter and catheter body which involves changes in physical parameters such as flexibility or lubricity from one end of the body to the other.

U.S. Pat. No. 5,533,985, to Wang, describes several configurations of differential stiffness tubing. This disclosure describes a differential stiffness multilayer tubing configuration embodiment wherein an outside layer and an inside layer both extend the full length of a catheter. A stiff material forms the inside layer which is significantly thicker in the proximal section than in the distal section, gradually decreasing in thickness toward the distal end. A soft material forms the outside layer which is significantly thinner in the proximal section than in the distal section, gradually increasing in thickness toward the proximal end. This configuration may be described as an inverse taper configuration wherein two layers taper inversely to produce a catheter of relatively constant overall thickness dimensions.

None of the documents cited above describe devices having the construction of the inventive catheter described below.

DESCRIPTION OF THE INVENTION

As noted above, this invention is a small diameter catheter which exhibits changes in mechanical properties along its length while maintaining favorable guidewire sliding properties throughout the inner lumen. The multilayer tubular catheter is formed using coextrusion technology which allows for simultaneous extrusion of multiple structural layers. The invention includes the method of controlling frictional and mechanical properties of the catheter during the coextusion process by changing specific variables involved.

Figure 1:
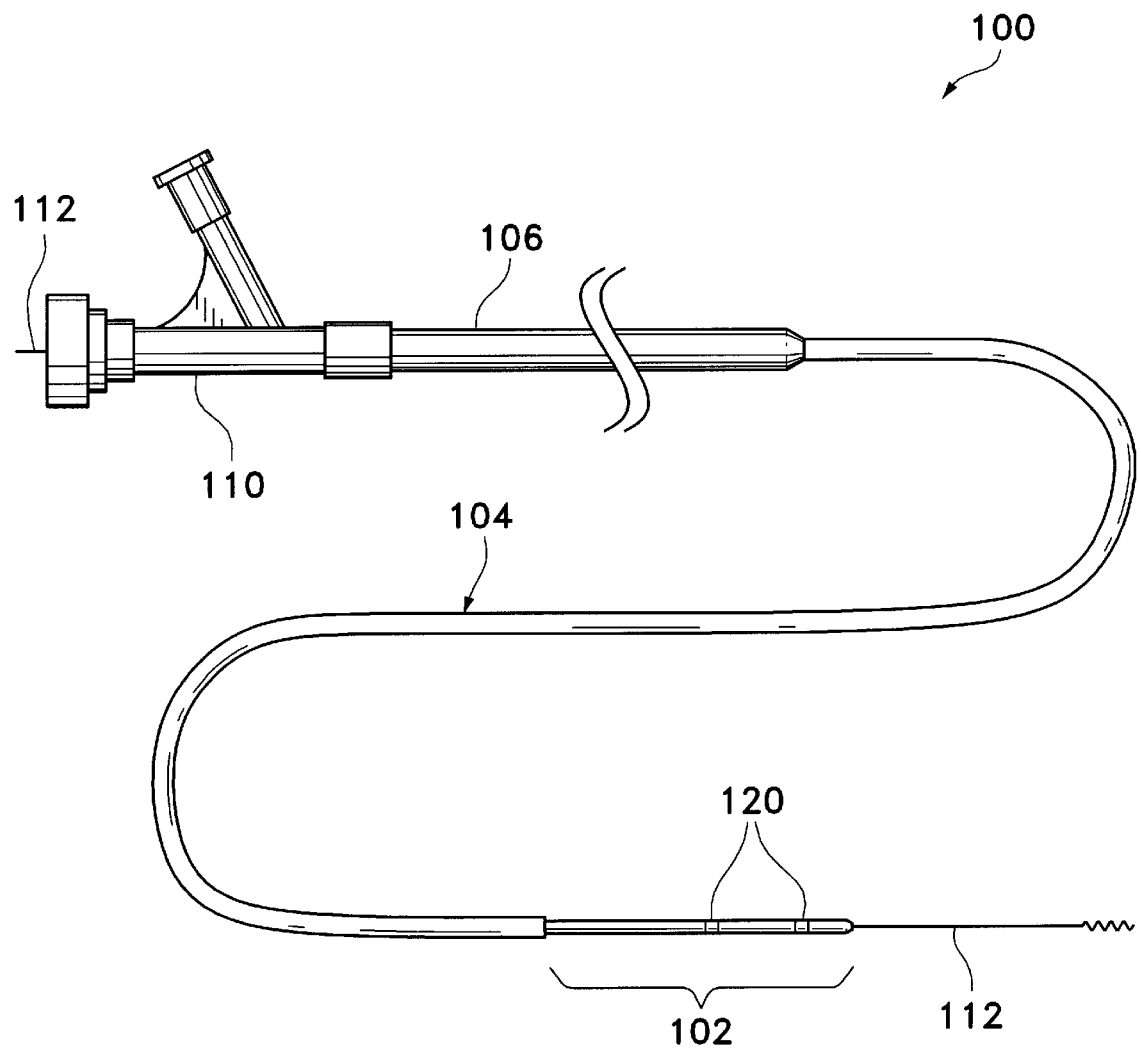
FIG. 1 shows, in side view, a typical three section catheter made according to this invention.

A typical multisection catheter which may incorporate the concepts of this invention is shown in FIG. 1. Such a catheter is suitable for use in both neurological and peripheral vascular applications, and is also suitable for less demanding service such as that which might be encountered in accessing and treating the heart. Higher demand for catheter access to remote regions of the body has resulted in specific performance constraints for catheters such as narrower diameters, longer lengths, greater flexibility, and facilitation of guidewire tracking when needed to reach certain regions of the body.

The inventive catheter (100) shown in FIG. 1 has a distal portion (102) having significant flexibility, a middle portion (104) having mechanical properties which vary from more flexible at the distal end of the portion to stiffer at the proximal end of the portion, and a proximal portion (106). The distal portion (102) is flexible and soft to allow deep penetration into the extraordinary convolutions of neurological vasculature without damaging the tissue walls of such lumens. In addition to having functionally designed overall mechanical properties, each of these portions is comprised of materials which facilitate low friction guidewire tracking. Various known and necessary accessories such as one or more radio-opaque bands (120) at the distal portion (102) to facilitate positioning of the catheter under fluoroscopy and a proximal assembly (110), or luer apparatus.

The typical dimensions of this catheter are 60–200 cm overall length, 60–150 cm proximal portion (106), and 2.5–50 cm distal portion (102). The outer diameter of the catheter desirably is between 0.008" and 0.120"; preferably between 0.010" and 0.060". The diameter of the inner lumen may be as small as 0.004". These dimensions are obviously selected as a function of the disease treatment site within the body, and the available pathways thereto.

Figure 2:
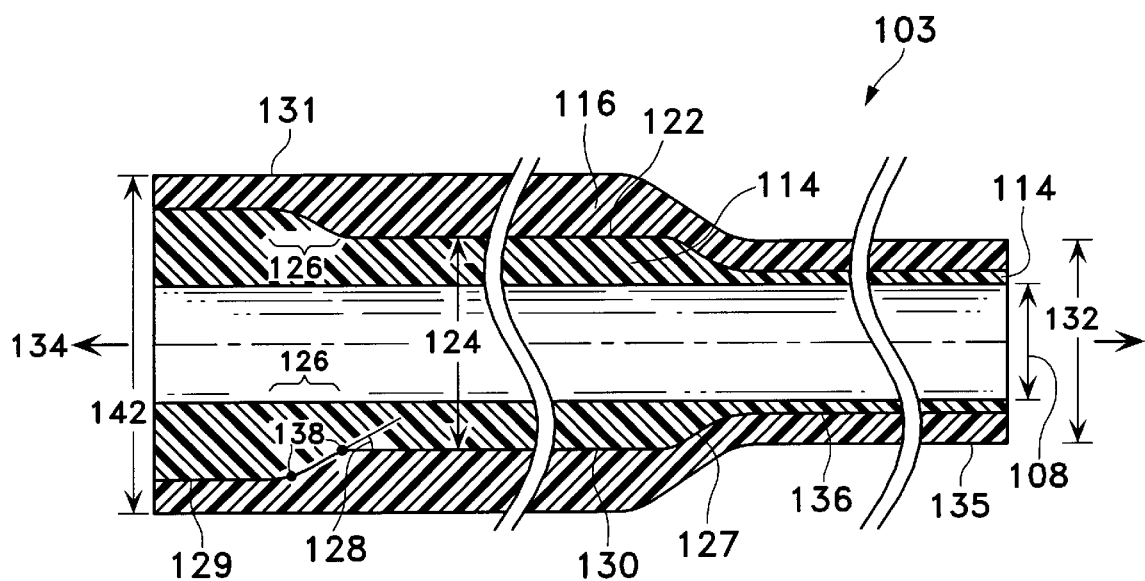
FIGS. 2, 3, 4, and 5 show, in magnification, fragmentary cross-sections of catheter sections made according to this invention.

FIG. 2 depicts a magnified section of a catheter body showing the aspects of one variation of the invention. Desirably, the more proximal portion (104) of the catheter body (103) has two layers, an inner layer (114) and an outer layer (116), which form a common wall and meet at an interface (122) measured by the interfacial diameter (124). In the preferred embodiment, the relative thicknesses of each of these layers (114, 116) is varied intermittently during the coextrusion process to produce three regions (125, 130, 136) of substantially constant interfacial diameter and two transition zones (126, 127) between those regions. The relative thicknesses of the inner (114) and outer layer (116), as well as the length of each region (125, 130, 136) of substantially constant interfacial diameter, the distal portion outer diameter (132), proximal portion outer diameter (142) dimensions, and the materials selection have critical roles in the mechanical performance of the catheter.

The quantity of change in interfacial diameter (124) and the rate of change thereof in relation to position along the longitudinal axis (134) of the catheter body (103) may define a transition angle (128). The transition angle roughly quantifies the geometry of the transition zone and can be used to describe transition zones which are not linear. For example, the transition zones (126, 127) depicted in FIG. 2 are not linear, but may be described with a transition angle using points of inflection (138) along the curve which defines the transition zone (126). The inventive catheter may have transition zones with transition angles anywhere in the range of 5 to 85 degrees.

The materials making up the catheter are typically polymeric and may be either neat or filled. The polymers may contain radio-opaque agents such as powdered tantalum or tungsten, barium sulfate, bismuth oxide, bismuth oxychloride, or bismuth carbonate. The term "filled" is also used in reference to materials which have additive elements such as colorants and reinforcing fibers, etc.

The polymers suitable for the catheters of this invention include thermoplastics such as low density polyethylene, high density polyethylene, polypropylene, ethyl vinylacetate, polystyrene, polyurethane, polyethylene terepthalate, polyesters such as the Nylons or Hytrel, or polyvinyl chloride. Lubricious polymers such as polyfluorocarbons or polysulfones are especially preferred due to their favorably low surface coefficients of friction. PTFE and FEP, in particular, are very useful fluoropolymers. Blends, alloys, copolymers of the noted polymers such as PEBAX or THV are also desirable. Due to the coextruded construction of the device and the desire to control mechanical and frictional properties using engaged yet separate layers of material, polymers which adhere to and are miscible with other polymers in their melt form are especially preferred. For instance, an inner layer of polyethylene terephthalate and an outer layer of polyurethane are preferred.

Central to this invention is the concept of maintaining inner lumen frictional properties while changing the mechanical behavior of the catheter shaft by varying the relative compositions of inner layer (114) and outer layer (116) materials in an intermittent fashion during the simultaneous coextrusion of the layers comprising the catheter body (103) wall. The engineering mechanics of hollow cylinders dictate that the materials farthest from the inner lumen may experience the largest stresses under bending and torsional loads, and will generally have significant effects on the overall stiffness of the catheter structure. Principles of mechanics similarly dictate that locations of structural inhomogeneity, such the transition zones (126, 127) in the inventive device where interfacial diameter (124) changes, may produce stress concentrations around these discrete locations. Such stress concentrations result in inhomogenious bending mechanics for the overall structure, and represent another source of mechanical property control for the structure designer.

Figure 3:
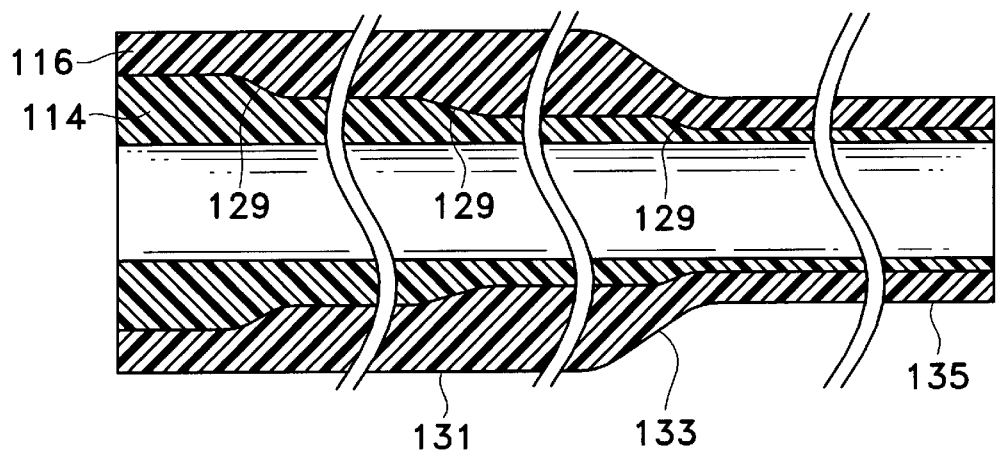
Figure 4:
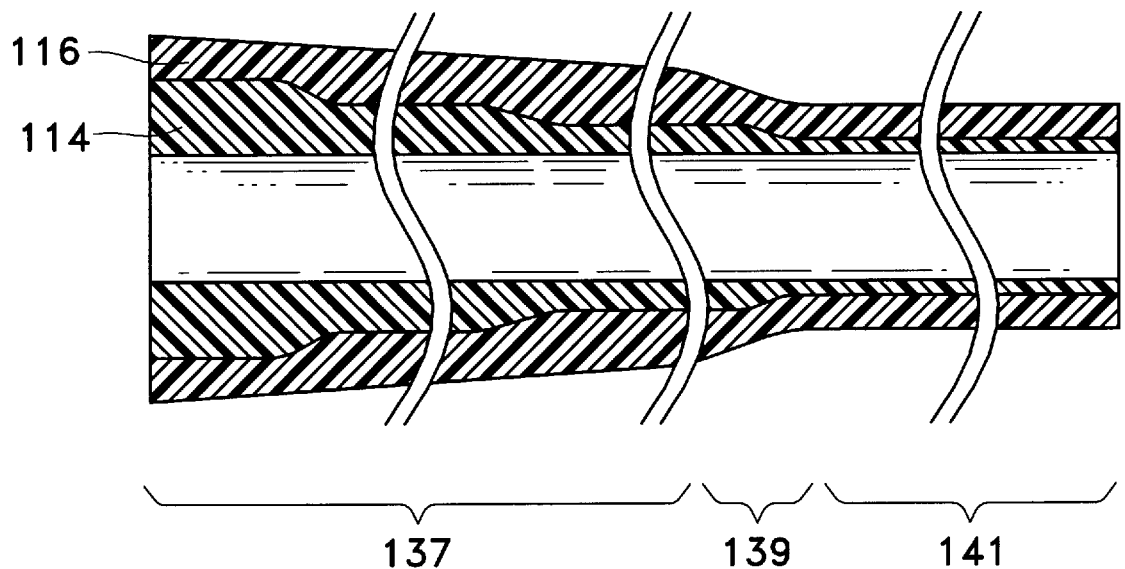
Figure 5:
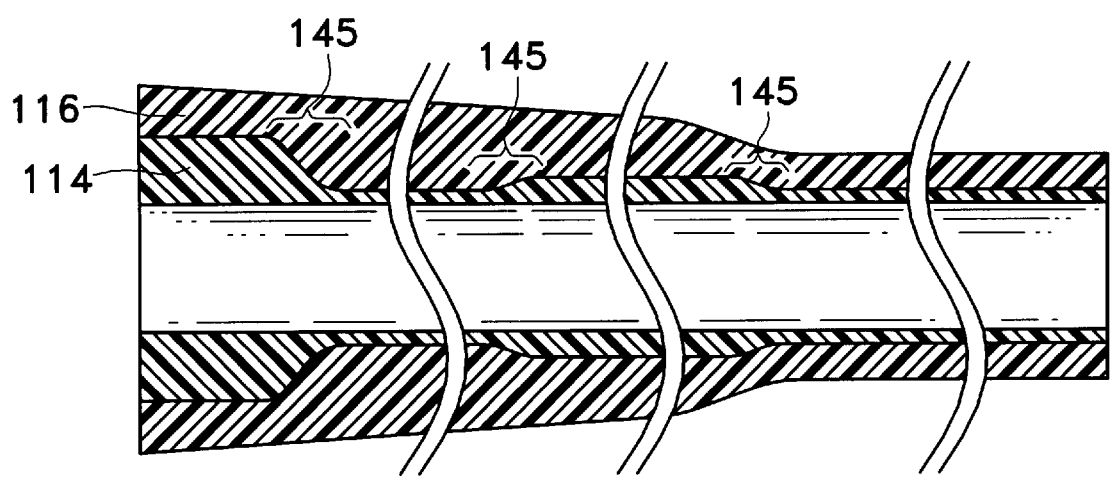

As a result of the desire to have highly controlled catheter structural mechanics which generally vary from more flexible distally to more rigid proximally as well as a inner layer (114) material which facilitates low friction guidewire passage, the inventive catheter employs a flexible outer layer (116) mechanically buffered by a stiffer inner layer (114). In addition to providing mechanical rigidity, the stiffer inner layer (114) material also is preferable as a puncture resistant and smooth bearing surface for guidewires (112) which may be used to guide the inventive device. In the preferred embodiment depicted in FIG. 2, the relative composition of relatively flexible outer layer (116) material increases proximally to distally in an intermittent pattern which results in two transition zones (126, 127). FIGS. 3, 4, and 5 depict, in fragmentary partial cross section, side views side views of various catheters made in accordance with this invention. It is inherent that the tensile modulus, also known as the modulus of elasticity or Young's modulus, of the stiffer inner layer (114) will be greater than the tensile modulus of the flexible outer layer (116), as the inner layer (114) is relatively stiffer than the flexible outer layer (116).

FIG. 3 depicts another embodiment of the inventive catheter which has three transition zones (129) and several regions of substantially constant interfacial diameter within the proximal portion (131). Like the preferred embodiment, the embodiment shown in FIG. 3 has a substantially constant outer diameter along the length of the proximal portion (131). The outer surface has one transition zone (133) to the substantially constant outer diameter of the distal portion (135). The additional transition zone and interfacial diameter step equates to more control variables along the length of the catheter which can be used to change the devices overall mechanical character. It is highly desirable in this variation and in the others shown herein, that the wall thickness of the inner layer (114) be very thin (e.g., 0.0025 to 0.0075") and substantially constant in that thickness over the length of the distal portion (135).

FIG. 4 depicts another embodiment of the inventive device wherein the outer diameter of the more proximal portion (137) is not substantially constant, but rather is tapered from a maximum outer diameter at the proximal end of the proximal portion (137) to a smaller outer diameter at the transition zone (139) between the proximal portion (137) and the distal portion (141). Although the device depicted in FIG. 4 uses a linear taper of the outer diameter, other obvious variations such as transition zones and regions of substantially constant outer diameter therebetween can also be used to control the mechanical properties of the device.

FIG. 5 depicts another embodiment of the inventive catheter wherein four regions (143) of substantially constant interfacial diameter are connected by transition zones (145), but the interfacial diameters are not decreased proximally to distally as in the preferred embodiment. FIG. 5, rather, depicts an embodiment wherein the interfacial diameter variation along the length of the catheter has been customized for particular mechanical properties.

PRODUCTION OF THE CATHETER BODY

Figure 6:
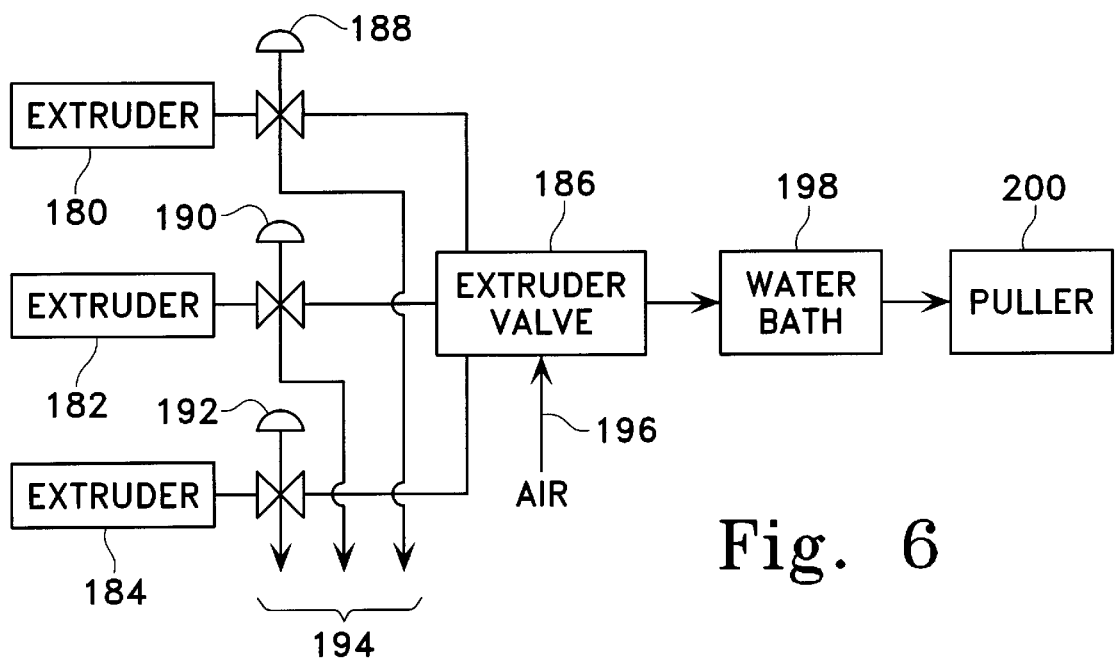
FIG. 6 shows a schematic outline of the extrusion apparatus suitable for creating the catheter.

The catheter body of this invention may be made according to the following procedure. A preferred device for producing these inventive catheters is schematically shown in FIG. 6. In this depiction, three extruders (180, 182, and 184) of typical design and configuration feed a single extruder head or die (186). The extruders may be of known design such as screw extruders and use, for instance, screws typically chosen for the polymers employed in the catheter body. Each of the extruders (180, 182, and 184) have control valves (188, 190, and 192) which may be operated either as proportional valves (partially opening) or as cut-off valves (being only either open or closed). The valves either supply the polymer to the extruder (186) or to a dump region (194), potentially for recycle. Air is supplied to the extruder head (186) desirably, independently for each catheter lumen extruded.

Figures 7A, 7B:
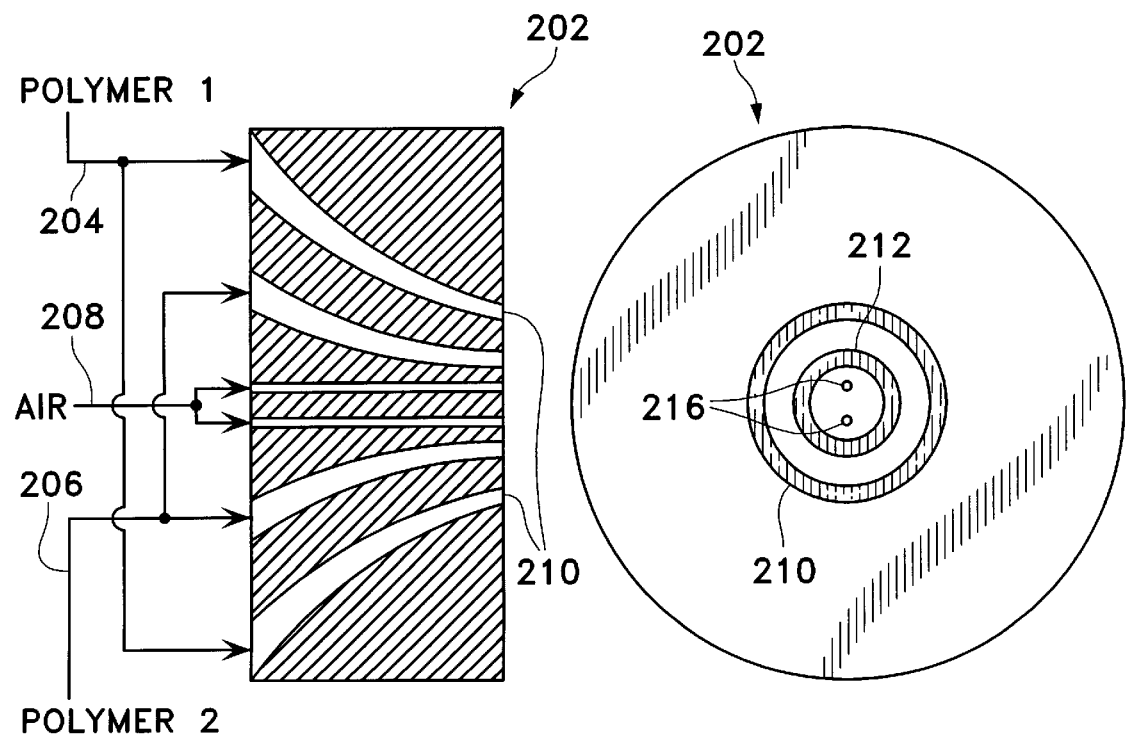
FIGS. 7A and 7B show, respectively, a side cross section of and an end view of an extrusion valve or die suitable for the production of the inventive catheter body.

The polymers from each extruder (180, 182, and 184) enter the extruder head (186), as desired, and exit through the die face, e.g., shown in FIG. 7B. The semi-molten catheter body is then pulled through a water bath (198) typically using a puller (200). The speed of the puller (200) and the pressure of the various extrusion air supplies (196) desirably are variable as needed.

FIG. 7A shows a side view, cross-section of an extrusion die (202) similar in concept to the die (186) in FIG. 6 but capable of handling only two polymer streams simultaneously—although various polymer streams may be mixed or otherwise controlled prior to reaching the die. In this instance, the outer layer of the catheter shaft is formed of a first polymer (204) and the inner layer is formed of a second polymer (206). The first polymer goes through an outer annular region (210) and the second polymer exits through an inner annular region (212) as well as a cross area (214) shown in FIG. 7B. Two independent air supplies (collectively 208) are shown.

FIG. 7B shows an end view of the extrusion die (202) found in FIG. 7A. Also shown are outer annular region (210) and the inner annular region (212). The orifices (collectively 216) for exit of the extrusion air are shown.

The invention has been described by description and by example. The examples are just examples and are not to be used to limit the scope of the invention in any way. Additionally, one having ordinary skill in this art will recognize variations and equivalents without the scope of the appended claims but are considered to be within the spirit of invention as described.

We claim as our invention:

1. A catheter in the form of an elongate tubular member, comprising:
   a. a proximal portion and a distal portion adjacent to said proximal portion;
   b. a longitudinal axis extending through said portions;
   c. a continuous polymeric outer layer extending between a proximal end of said proximal portion and a distal end of said distal portion, said continuous outer layer having a proximal portion outer diameter and a distal portion outer diameter wherein said distal portion outer diameter is substantially constant along the length of said distal portion and is smaller than said proximal portion outer diameter;

d. a continuous polymeric inner layer extending between the proximal end of said proximal portion and the distal end of said distal portion, said inner layer defining an inner lumen;

e. an interface between said inner and outer layers, the interface having a diameter that varies intermittently along said longitudinal axis forming at least three continuous regions of constant interfacial diameter, each of said continuous regions having a different diameter.

2. The catheter of claim 1 further comprising a transition zone between each of the adjacent regions of constant interfacial diameter wherein the interfacial diameter decreases in a proximal to distal direction.

3. The catheter of claim 1 wherein the rate of decrease of the interfacial diameter in the transition zone as a function of distance along the longitudinal axis for each of the regions of constant interfacial diameter is constant, thereby defining a transition angle.

4. The catheter of claim 3 wherein the transition angle is between 85 and 5 degrees.

5. The catheter of claim 1 wherein said inner layer and said outer layer are coextruded simultaneously.

6. The catheter of claim 1 further comprising a removable, slideable guidewire placed interior to and in slideable relationship with said portions.

7. The catheter of claim 1 wherein at least one of said inner layer and said outer layer is radio-opaque.

8. The catheter of claim 1 wherein the outer layer comprises a polymer selected from low density polyethylene, ethylvinylacetate, polyethylene terepthalate and their mixtures and copolymers.

9. The catheter of claim 1 wherein the inner layer comprises a polymer selected from polyimide, polyamides, high density polyethylene, polypropylene, fluoropolymers including PTFE, FEP, vinylidene flouride, and their mixtures, alloys, copolymers, and block copolymers, polysulfones or the like.

10. The catheter of claim 9 wherein the polymeric inner layer has a wall thickness of 0.0025 inches to 0.0075 inches.

11. The catheter of claim 1 wherein the distal end of the distal portion has an outer diameter less than 0.010 inches.

12. The catheter of claim 1 wherein said outer diameter is substantially constant along the length of the proximal portion.

13. The catheter of claim 1 wherein said outer diameter varies along the length of the proximal portion.

14. The catheter of claim 13 wherein said outer diameter varies along the length of the proximal portion with a tapered pattern wherein said outer diameter is largest at the proximal end of said proximal portion, and smallest at the distal end of said proximal portion.

15. The catheter of claim 1 further comprising a proximal assembly attached to the proximal end of said proximal portion, wherein said proximal assembly is designed to facilitate guidewire and fluids access.

16. The catheter of claim 1, said distal portion having a constant outer diameter and a constant inner lumen diameter.

17. The catheter of claim 1 wherein said inner layer comprises a material with a higher tensile modulus than that of the material which comprises said outer layer.

18. The catheter of claim 1 wherein the polymeric inner layer has a wall thickness of 0.0025 inches to 0.0075 inches.

* * * * *

UNITED STATES PATENT AND TRADEMARK OFFICE
CERTIFICATE OF CORRECTION

PATENT NO. : 6,030,369
DATED : February 29, 2000
INVENTOR(S) : Erik T. ENGELSON and Mark CARTER It is certified that error appears in the above-indentified patent and that said Letters Patent is hereby corrected as shown below:

In column 1, line 29, please replace "these" with --there--;

In column 5, line 22, please replace "a" with --an--; and

In column 5, line 51, please replace "devices" with --device's--.

Signed and Sealed this

Thirteenth Day of March, 2001

NICHOLAS P. GODICI

*Attest:*

*Attesting Officer*  *Acting Director of the United States Patent and Trademark Office*